(12) United States Patent
Unger et al.

(10) Patent No.: US 9,201,032 B2
(45) Date of Patent: Dec. 1, 2015

(54) GAS SENSOR

(71) Applicant: Dräger Safety AG & Co. KGaA, Lübeck (DE)

(72) Inventors: Jürgen Unger, Berlin (DE); Mladen Schlichte, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 13/761,630

(22) Filed: Feb. 7, 2013

(65) Prior Publication Data
US 2013/0202490 A1    Aug. 8, 2013

(30) Foreign Application Priority Data
Feb. 8, 2012   (DE) .......................... 10 2012 002 456

(51) Int. Cl.
| | |
|---|---|
| *G01N 15/06* | (2006.01) |
| *G01N 33/00* | (2006.01) |
| *G01N 33/48* | (2006.01) |
| *G01N 25/32* | (2006.01) |

(52) U.S. Cl.
CPC ...................................... *G01N 25/32* (2013.01)

(58) Field of Classification Search
USPC ..................................... 422/83, 94, 95, 96, 98
See application file for complete search history.

(56) References Cited

U.S. PATENT DOCUMENTS

| | | |
|---|---|---|
| 5,018,395 A | 5/1991 | Hickox et al. |
| 7,426,849 B2 | 9/2008 | Lange et al. |
| 2003/0127325 A1 | 7/2003 | Khesin et al. |
| 2005/0229675 A1 | 10/2005 | Haupt et al. |
| 2006/0243029 A1 | 11/2006 | Lange et al. |
| 2011/0158854 A1 | 6/2011 | Yamagishi et al. |

FOREIGN PATENT DOCUMENTS

| | | |
|---|---|---|
| CN | 86106172 A | 6/1987 |
| CN | 1399720 A | 2/2003 |
| CN | 1434293 A | 8/2003 |
| CN | 200989890 Y | 12/2007 |
| DE | 691 24 021 T2 | 4/1997 |
| DE | 29 823 367 U1 | 5/1999 |
| DE | 10 2004 019008 A1 | 11/2005 |
| DE | 10 2005 020131 B3 | 5/2006 |
| DE | 10 2010 053366 A1 | 6/2011 |
| DE | 10 2011 010074 A1 | 8/2012 |
| GB | 1122430 A | 8/1968 |
| GB | 1358368 A | 7/1974 |

*Primary Examiner* — Brian J Sines
(74) *Attorney, Agent, or Firm* — McGlew and Tuttle, P.C.

(57) ABSTRACT

A gas sensor for detecting combustible gases is provided with a catalytic sensor element. The catalytic sensor element is arranged in a housing (1) surrounding the catalytic sensor element on all sides. The housing has a gas-permeable inlet opening. The gas sensor has electric lines, which are in connection with the sensor element and have terminals located outside of the housing (1). The housing has a gas-permeable inlet opening (2) and a gas-permeable outlet opening (3) and a flow channel (4) connecting the gas-permeable inlet opening (2) and the gas-permeable outlet opening (3). The sensor element is arranged in the flow channel.

20 Claims, 4 Drawing Sheets

GAS SENSOR

CROSS REFERENCE TO RELATED APPLICATIONS

This application claims the benefit of priority under 35 U.S.C. §119 of German Patent Application DE 10 2012 002 456.8 filed Feb. 8, 2012, the entire contents of which are incorporated herein by reference.

FIELD OF THE INVENTION

The present invention pertains to a gas sensor for detecting combustible gases with a catalytic sensor element, which is heated during operation and is arranged in a housing enclosing it on all sides, which has a gas-permeable inlet opening, and with electric lines, which are in connection with the sensor element and have terminals located outside the housing.

BACKGROUND OF THE INVENTION

Such a gas sensor is known, for example, from DE 10 2005 020 131 B3 (corresponding to U.S. Pat. No. 7,426,849). Such gas sensors operate with catalytic oxidation of combustible gases, which leads to a rise in temperature at the sensor element, which in turn entails a change in the resistance of the sensor element, which can be measured from the outside via the terminals. Such gas sensors are used, for example, to detect explosive gas mixtures. The sensor element is heated here electrically to a relatively high operating temperature (up to approximately 500° C.). When a combustible gas is present at the surface of the sensor element, this gas is oxidized and a change in the surface temperature of the sensor element is brought about by the heat generated. The gas sensor known from DE 10 2005 020 131 B3 has a housing with a gas inlet opening. The gas inlet opening is closed with a gas-permeable closure, which is said to act as a flame arrester and to prevent hereby flames from being able to break through to the outside in the presence of combustible gases. The closure consists of, e.g., wire mesh or sintered metal bodies. A second sensor element, which does not come into contact with the ambient atmosphere, may be provided. A comparison of the changes in the resistances of the first sensor element and the second sensor element makes it therefore possible to infer which temperature change can be attributed to the oxidation of combustible gas, e.g., by comparing the voltages over the two sensor elements via a Wheatstone bridge. The sensor elements are connected to lines in the form of metal pins, which lead out of the housing of the gas sensor. The lines are passed through openings in the housing of the gas sensor, which are closed with glass seals. The combustible gas to be detected enters this gas sensor through the gas-permeable closure in the inlet opening by diffusion and thus reaches the sensor element in the interior of the container. The gas transport to the reaction element takes place by diffusion and by incidentally occurring changes in the ambient conditions, e.g., due to wind flows. However, the latter may sometimes also have opposite effects, namely, they may hinder the diffusion of the gas molecules to the sensor element.

The consequence of the above-described mode of operation of the gas sensor is a relatively long response time of the gas sensor during the detection of the target gas or target gases. The response times depend, moreover, on the gas species. It is also disadvantageous in respect to the response time that the combustion products of the combustible gas, which arise from the function, collect in the interior of the housing and may hinder as a result the diffusion of the combustible gases to be detected towards the sensor element.

SUMMARY OF THE INVENTION

An object of the present invention is to improve a gas sensor of the type mentioned in the introduction such that the response time for the detection of the combustible gases is shortened and the sensitivity of the gas sensor is increased by a better gas exchange Furthermore, the effect of combustion products on the diffusion of the combustible gas towards the sensor element shall be reduced or prevented altogether.

According to the invention, a gas sensor is provided for detecting combustible gases. The gas sensor comprises a catalytic sensor element, which is heated during the operation and a housing defining a flow channel. The catalytic sensor element is arranged in the housing and encloses the catalytic sensor element on all sides. The housing has a gas-permeable inlet opening and a gas-permeable outlet opening. The flow channel connects the gas-permeable inlet opening and the gas-permeable outlet opening. Electric lines connect with the sensor element. The electric lines have terminals located outside of the housing. The flow channel has a first cylindrical section, with a first greatest cross sectional dimension, and a second cylindrical section located vertically above the first cylindrical section, with a second greatest cross sectional dimension. The first dimension is greater than the second dimension, in order to enhance a convective flow from the bottom through the inlet opening upwardly and through the outlet opening.

Provisions are made according to the present invention for a gas-permeable outlet opening located opposite the inlet opening being provided in the housing. The gas-permeable inlet opening is connected by the flow channel to the gas-permeable outlet opening. The sensor element is arranged in the flow channel. A gas flow, which allows gas to flow from the ambient atmosphere into the inlet opening, through the flow channel in the housing and through the outlet opening again into the surrounding area, is generated in this manner by convection. On the one hand, a short response time is obtained in this manner. In addition, possible combustion products are removed by the gas flow from the interior of the housing, so that combustion products cannot accumulate any more.

The gas-permeable inlet opening is arranged in the housing of the gas sensor in a preferred embodiment such that it opens downwardly in the operating position of the gas sensor.

The gas-permeable inlet opening, flow channel and gas-permeable outlet opening are preferably arranged in the housing such that the flow channel extends vertically from bottom to top through the housing in the operating position of the gas sensor. The heat generated by the sensor element ensures a convective flow through the housing, so that the heated sensor element is located in the convective flow of gas through the flow channel However, the flow channel does not have to extend exactly vertically in the operating position of the gas sensor; a convective flow is rather generated already when the gas-permeable inlet opening is positioned vertically below the gas-permeable outlet opening in the operating position of the gas sensor.

In a preferred embodiment, the flow channel has a first cylindrical section with a first diameter or first largest dimension and a second cylindrical section located vertically above it with a second diameter or second largest dimension, wherein the first diameter is greater than the second diameter. The flow channel has a first (lower) flow cross section that is greater than a second (upper) flow cross section.

The diameter of the first cylindrical section of the flow channel is preferably greater than 10 μm.

In a preferred embodiment, the length of the flow channel through the housing is greater than 2 mm.

The gas-permeable inlet opening is preferably closed with a gas-permeable closure made of sintered metal or woven steel wires.

In a preferred embodiment, the gas-permeable outlet opening is closed with a closure made of sintered metal or woven steel wires.

The present invention will be described below on the basis of exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
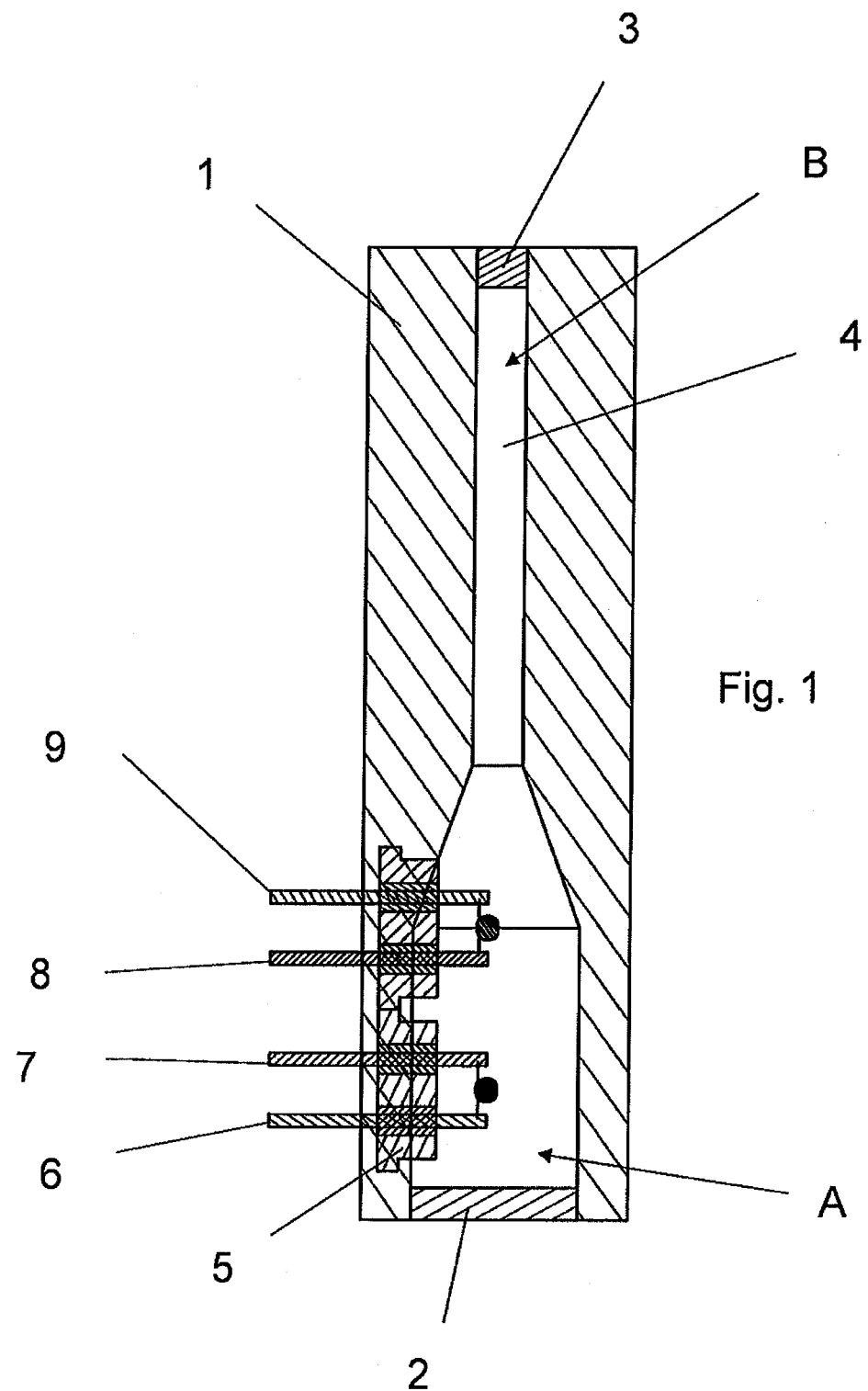
FIG. 1 is a schematic cross-sectional view of a gas sensor according to a first embodiment of the invention.

Referring to the drawings in particular, FIG. 1 shows a cross-sectional view of a gas sensor. The gas sensor has a housing 1 and a gas-permeable inlet opening 2 located at the bottom at the housing. A gas flow channel 4 extends from gas inlet opening 2 to a gas-permeable outlet opening 3 at the top at housing 1. Flow channel 4 has, following gas inlet opening 2, a first cylindrical section A with a first diameter, which is joined by a second cylindrical section B with a smaller diameter, which leads to the gas-permeable outlet opening 3. A first sensor element and a second sensor element are arranged in lower section A of flow channel 4, one sensor element being in contact with the atmosphere in the flow channel and the other sensor element not having any contact with the atmosphere in the flow channel, for which purpose one of the sensor elements is enclosed with a capsule (not shown). The second sensor element is thus used as a reference. The first sensor element is provided with metal pins 6, 7, which extend from the first sensor element in the interior of the housing through a seal 5 in the housing to the outside. The second sensor element is provided with metal pins 8, 9, which likewise extend from the interior of the housing towards the outside. The voltages between the metal pins 6, 7 and 8, 9 are sent to a measuring circuit, for example, a bridge circuit, such as a Wheatstone bridge, which sends a bridge signal, which is a measure of the concentration of the target gas being sought.

The first cylindrical section A with the greater diameter passes over a conical intermediate section into the second cylindrical section B with a smaller diameter. This shape reinforces the convective flow from the bottom through the inlet opening 2 in the upward direction through outlet opening 3 out of housing 1. The flow channel extends vertically upwardly from the bottom through housing 1.

Figure 2:
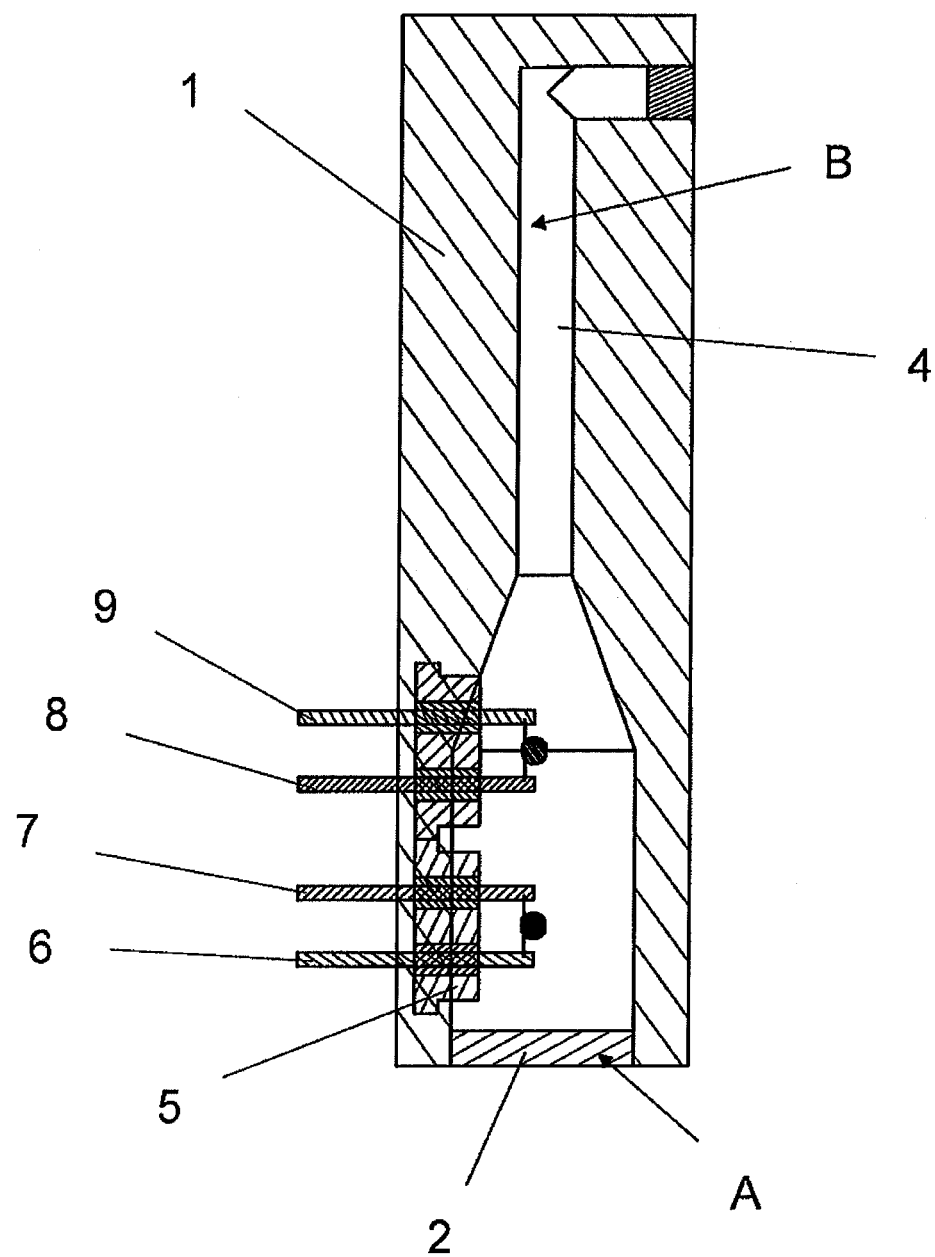
FIG. 2 is a schematic cross-sectional view of a gas sensor according to a second embodiment of the invention.

FIG. 2 shows an alternative embodiment of a gas sensor, wherein outlet opening 3 is not arranged pointing upwards at the housing, but it leads out of housing 1 laterally at the upper end. Sufficient convective flow, which guarantees rapid response of the gas sensor and prevents combustion products from accumulating, is obtained in this embodiment as well.

Figure 3:
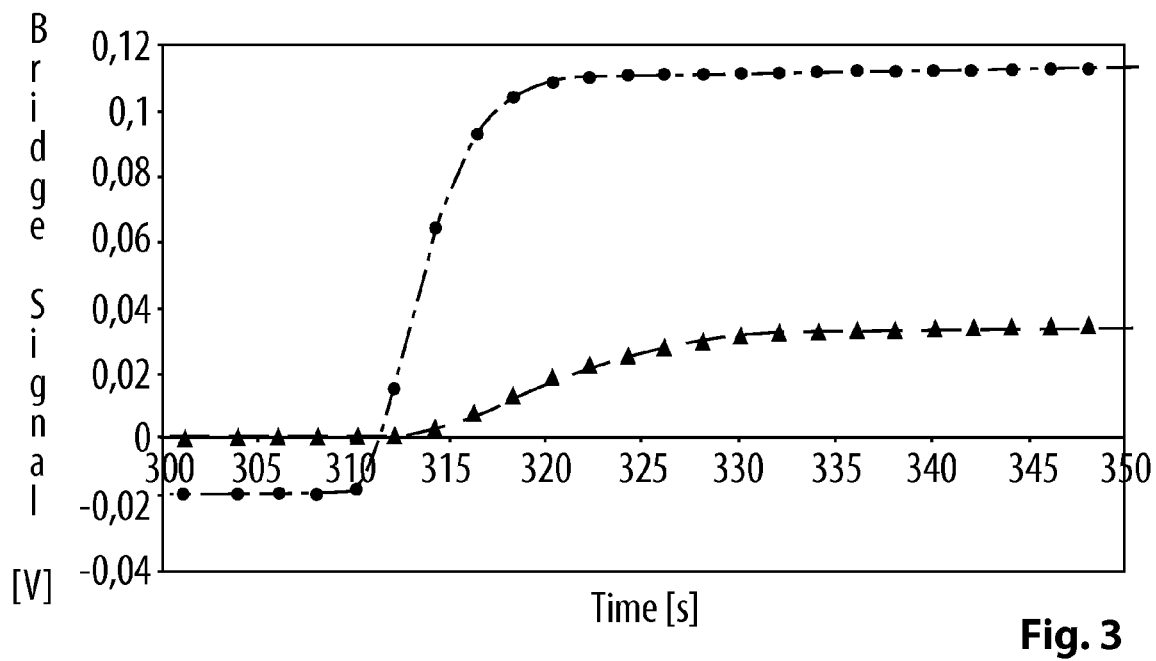
FIG. 3 is a diagram showing the gas sensor signal as a function of time when the ambient atmosphere of the gas sensor is set at 50% of the LEL (LEL=lower explosion limit)

The improved mode of operation of the gas sensor according to the present invention will now be explained on the basis of FIGS. 3 through 5, in which a gas sensor according to the present invention is compared with a conventional gas sensor. FIG. 3 shows the changes in the measured signal of a gas sensor according to the present invention over time with the dots, while the measured signal of a conventional gas sensor is represented with triangles for comparison. FIG. 3 shows the transition from an atmosphere free from combustible gases to an ambient atmosphere containing a percentage of propane corresponding to 50% of the LEL (LEL=lower explosion limit). FIG. 3 shows that the gas sensor according to the present invention rises much faster to a saturated signal than is the case with a conventional gas sensor shown for comparison after adding propane at a concentration corresponding to 50% of the LEL (LEL=lower explosion limit). This proves that the change in the ambient atmosphere leads to the corresponding change in the sensor signal much faster due to the convective flow through the housing.

Figure 4:
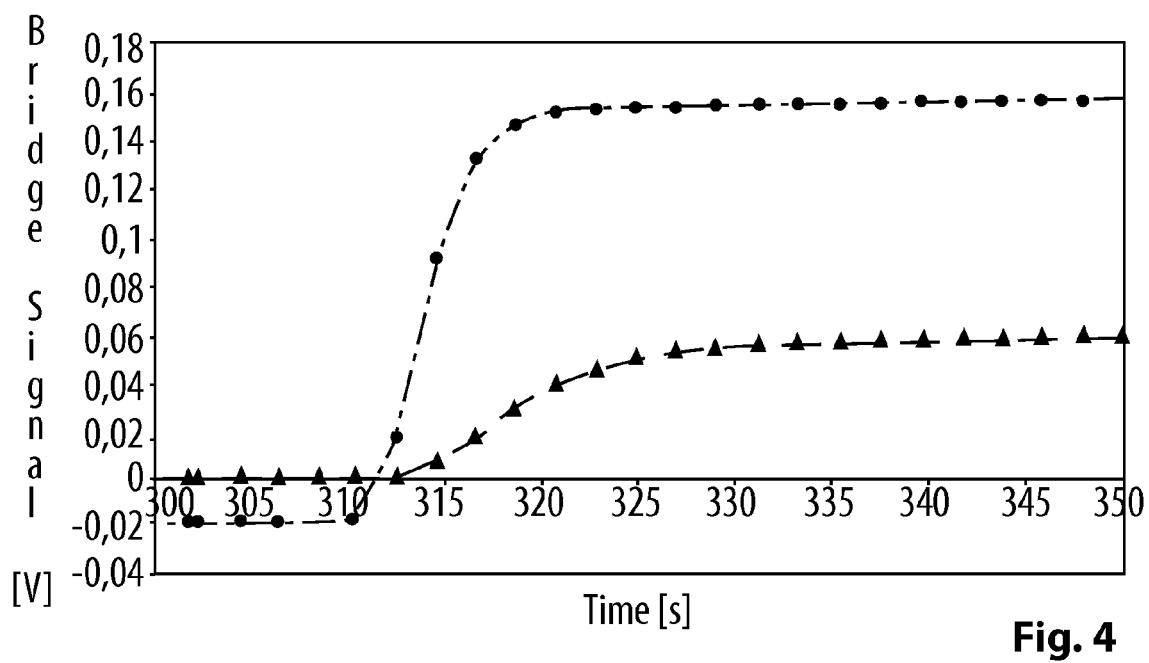
FIG. 4 shows the gas sensor signal as a function of time when the ambient atmosphere of the gas sensor is set at 50% of the LEL of methane (LEL=lower explosion limit)

FIG. 4 shows another example of the gas sensor signal as a function of time during the transition from an ambient atmosphere free from combustible gases to an atmosphere containing methane at a concentration corresponding to 50% of the LEL. The sensor signal of the gas sensor according to the present invention is represented here by circles and the signal of the conventional gas sensor by triangles. The markedly faster response characteristic of the gas sensor according to the present invention is seen here as well.

Figure 5:
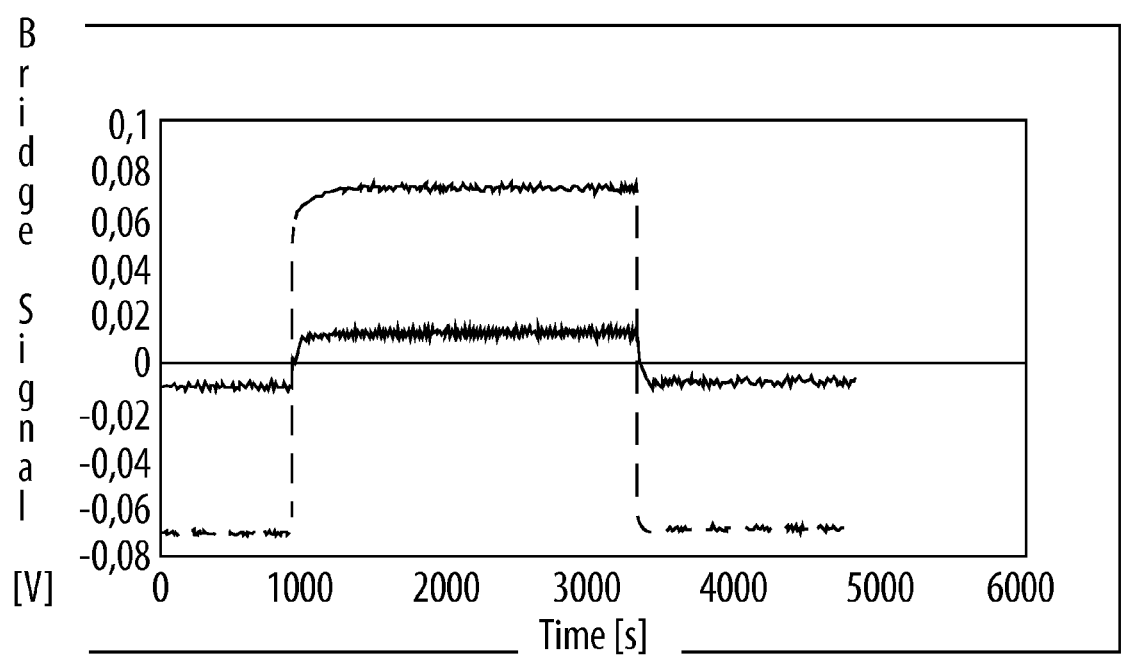
FIG. 5 shows the gas sensor signal as a function of time when the ambient atmosphere is set at 50% of the LEL of nonane and subsequent return to an ambient atmosphere without combustible gases.

FIG. 5 shows another comparison example between a gas sensor according to the present invention (measured signal indicated by broken line) and a conventional gas sensor (solid line). A transition from an ambient atmosphere without combustible gases to an atmosphere containing nonane at a concentration corresponding to 50% of the LEL and subsequently a transition again to an ambient atmosphere free from combustible gases is shown. It shall be noted here that, just as in FIGS. 3 and 4, only the amount of rise of the signal is important here, i.e., measured signals<0 in an ambient atmosphere free from combustible gas mean lack of compensation of the bridge circuit.

While specific embodiments of the invention have been shown and described in detail to illustrate the application of the principles of the invention, it will be understood that the invention may be embodied otherwise without departing from such principles.

What is claimed is:

1. A gas sensor for detecting combustible gases, the gas sensor comprising:
   a catalytic sensor element, which is heated during operation;
   a housing defining a flow channel, the housing enclosing the catalytic sensor element on all sides, the housing having a gas-permeable inlet opening and a gas-permeable outlet opening, the flow channel connecting the gas-permeable inlet opening and the gas-permeable outlet opening; and electric lines connected with the sensor element, the electric lines having terminals located outside of the housing, the flow channel having a first cylindrical section with a first greatest cross sectional dimension, a second cylindrical section located vertically above the first cylindrical section with a second greatest cross sectional dimension and a conical section, said catalytic sensor being arranged in said first cylindrical section, said first cylindrical section being connected to said second cylindrical section via said conical section, wherein the first dimension is greater than the second dimension, in order to enhance a convective flow from the bottom through the inlet opening upwardly and through the outlet opening.

2. A gas sensor in accordance with claim 1, wherein the inlet opening is defined by the housing such that the inlet opening opens downwardly in an operating position of the gas sensor, said first cylindrical section and said conical section defining at least a portion of a reaction chamber.

3. A gas sensor in accordance with claim 2, wherein the gas-permeable inlet opening, the flow channel and the gas-permeable outlet opening are arranged such that the flow channel extends vertically from a bottom upwards through the housing in an operating position of the gas sensor.

4. A gas sensor in accordance with claim 1, wherein the first dimension is greater than 10 µm.

5. A gas sensor in accordance with claim 1, wherein a length of the flow channel through the housing is greater than 2 mm.

6. A gas sensor in accordance with claim 1, further comprising a gas-permeable closure made of sintered metal or woven steel wires wherein the gas-permeable inlet opening is closed with the gas-permeable closure.

7. A gas sensor in accordance with claim 1, wherein the gas-permeable outlet opening is closed with a gas-permeable closure made of sintered metal or woven steel wires.

8. A gas sensor comprising:
a catalytic sensor element, which is heated during operation;
a housing defining a flow channel with an inlet opening and an outlet opening, the catalytic sensor element being arranged in the flow channel, the flow channel having a first flow section, between the inlet opening and the outlet opening, with a first flow cross section and the flow channel having a second flow section, between the inlet opening and the outlet opening, with a second flow cross section, and the flow channel having a conical flow section located between the first flow section and the second flow section, the second flow section being located vertically above the first flow section and the first flow cross section being greater than the second flow cross section, in order to enhance a convective flow from the inlet opening to the outlet opening; and
electric lines connected with the sensor element inside the housing and having terminals located outside of the housing.

9. A gas sensor in accordance with claim 8, wherein the inlet opening is defined by the housing such that the inlet opening opens downwardly in an operating position of the gas sensor, said catalytic sensor element being disposed in said first flow section, said second flow section being located vertically above the conical flow section, at least said first flow section and said conical flow section defining a reaction chamber.

10. A gas sensor in accordance with claim 9, wherein the inlet opening, the flow channel and the outlet opening are arranged such that the flow channel extends vertically from a bottom upwards through the housing in an operating position of the gas sensor, said conical flow section comprising a first conical flow cross section at one end thereof and a second conical flow cross section at another end thereof, said first conical flow cross section being equal to the first flow cross section, said second conical flow being equal to said second flow cross section.

11. A gas sensor in accordance with claim 8, wherein the first flow cross section has a minimum dimension that is greater than 10 µm.

12. A gas sensor in accordance with claim 8, wherein a length of the flow channel from the inlet opening to the outlet opening is greater than 2 mm.

13. A gas sensor in accordance with claim 8, further comprising an inlet gas permeable element closing the inlet opening, the inlet gas permeable element being formed of a sintered metal or woven steel wires.

14. A gas sensor in accordance with claim 8, further comprising an outlet gas permeable element closing the outlet opening, the outlet gas permeable element being formed of a sintered metal or woven steel wires.

15. A gas sensor comprising:
a catalytic sensor element, which is heated during operation;
a housing defining a flow channel with an inlet opening and an outlet opening, the catalytic sensor element being arranged in the flow channel, the flow channel having a first flow section, between the inlet opening and the outlet opening, with a first flow cross section and the flow channel having a second flow section, between the inlet opening and the outlet opening, with a second flow cross section, the flow channel having a third flow section, between the inlet opening and the outlet opening, with a third flow cross section, the second flow section being located vertically above the first flow section and the third flow section and the first flow cross section being greater than the second flow cross section, in order to enhance a convective flow from the inlet opening to the outlet opening, said third flow section comprising a first end portion located adjacent to said first flow section and a second end portion located adjacent to said second flow section, said third flow cross section decreasing from said first end portion to said second end portion;
an inlet gas permeable element closing the inlet opening;
an outlet gas permeable element closing the outlet opening, the catalytic sensor element being enclosed on all sides by the housing in cooperation with the inlet gas permeable element and the outlet gas permeable element; and
electric lines connected with the sensor element inside the housing and having terminals located outside of the housing.

16. A gas sensor in accordance with claim 15, wherein the inlet opening is defined by the housing such that the inlet opening opens downwardly in an operating position of the gas sensor, said third flow section being a conical flow section, said catalytic sensor element being disposed in said first flow section.

17. A gas sensor in accordance with claim 16, wherein the inlet opening, the flow channel and the outlet opening are arranged such that the flow channel extends vertically from a bottom upwards through the housing in an operating position of the gas sensor, said first end portion comprising a first conical flow cross section and said second end portion comprising a second conical flow cross section, said first conical flow cross section being equal to the first flow cross section, said second conical flow cross section being equal to said second flow cross section, whereby said first conical flow cross section is greater than said second conical flow cross section, said conical flow section and said first flow section defining at least a portion of a reaction chamber.

18. A gas sensor in accordance with claim 15, wherein the first flow cross section has a minimum dimension that is greater than 10 μm.

19. A gas sensor in accordance with claim 15, wherein a length of the flow channel from the inlet opening to the outlet opening is greater than 2 mm.

20. A gas sensor in accordance with claim 15, wherein:
   the inlet gas permeable element is formed of a sintered metal or woven steel wires; and
   the outlet gas permeable element is formed of a sintered metal or woven steel wires.

\* \* \* \* \*